United States Patent [19]

Sabot

[11] Patent Number: 4,483,801

[45] Date of Patent: Nov. 20, 1984

[54] PREPARATION OF SULFONATED TRIARYLPHOSPHINES

[75] Inventor: Jean-Louis Sabot, Maisons Laffitte, France

[73] Assignee: Rhone-Poulenc Chimie de Base, Courbevoie, France

[21] Appl. No.: 527,859

[22] Filed: Aug. 30, 1983

[30] Foreign Application Priority Data

Aug. 31, 1982 [FR] France .................. 82 14862

[51] Int. Cl.$^3$ .................................. C07C 143/24
[52] U.S. Cl. ............................ 260/505 C; 260/505 R
[58] Field of Search ..................... 260/505 R, 505 C

[56] References Cited

FOREIGN PATENT DOCUMENTS 2627354 12/1976 Fed. Rep. of Germany ...... 260/505

*Primary Examiner*—Alan Siegel
*Attorney, Agent, or Firm*—Burns, Doane, Swecker & Mathis

[57] ABSTRACT

Sulfonated triarylphosphines well suited for catalysis are facilely prepared by (i) sulfonating the aromatic moieties of a corresponding triarylphosphine starting material with an $H_2SO_4/SO_3$ mixture; (ii) hydrolyzing the sulfonation reaction mixture to terminate said sulfonation reaction when same has attained the desired degree of sulfonation, thereby producing a hydrolysate rich in sulfuric acid and which comprises the product sulfonated triarylphosphine; (iii) next liquid/liquid extracting said hydrolysate with an organic phase comprising at least one phosphoric or diphosphoric, phosphonic or diphosphonic, phosphinic or diphosphinic ester, or phosphine oxide or diphosphine dioxide, or slightly water miscible or immiscible $C_4$–$C_{12}$ alcohol, or sulfoxide extractant, whereby the sulfonated triarylphosphine is extracted into said organic phase, (iv) separating the organic phase from the aqueous raffinate; (v) regenerating said organic phase with water or with an aqueous solution; and (vi) recovering an aqueous solution of said sulfonated triarylphosphine.

25 Claims, 1 Drawing Figure

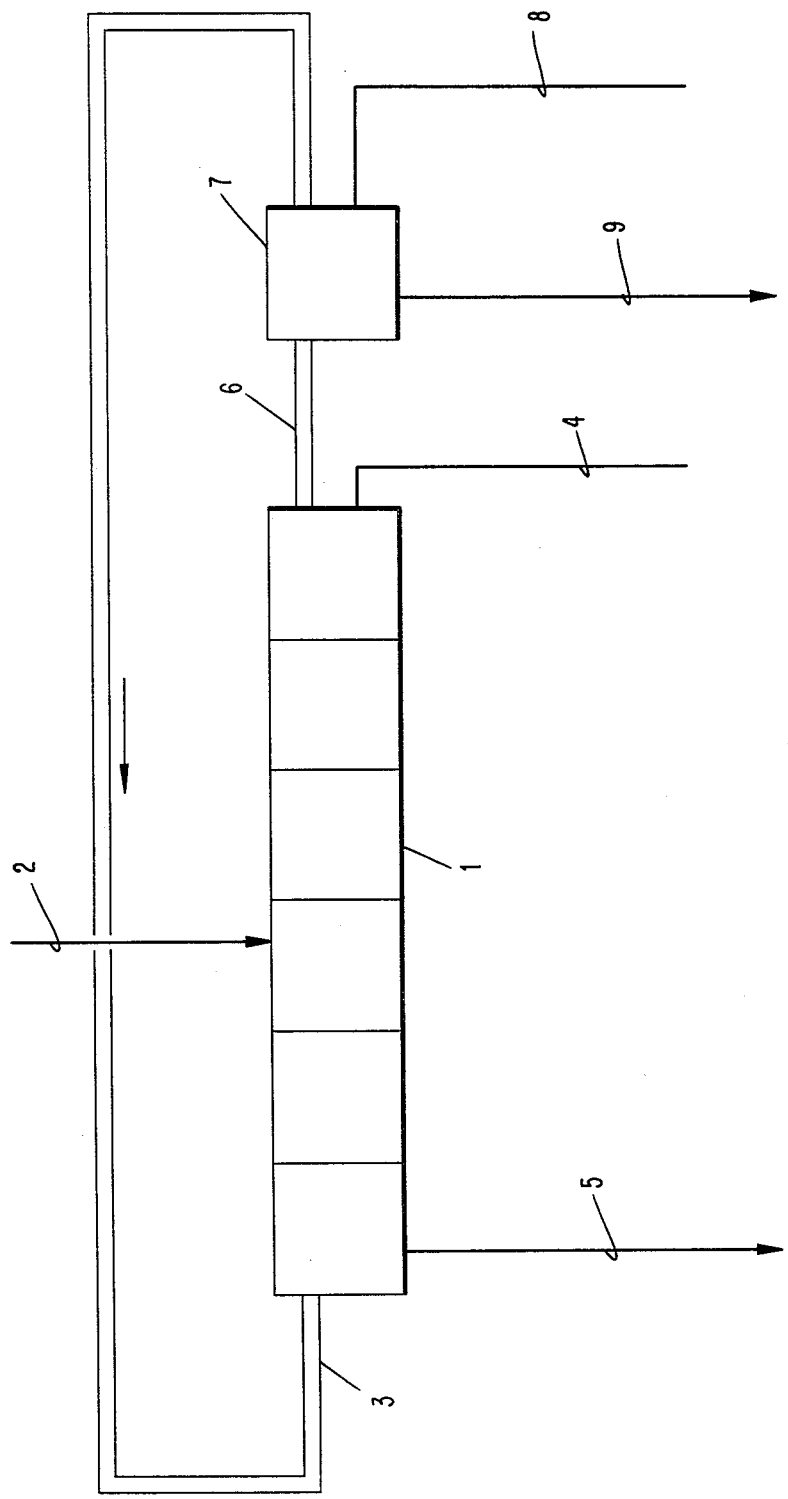

PREPARATION OF SULFONATED TRIARYLPHOSPHINES

BACKGROUND OF THE INVENTION

1. Field of the Invention:

The present invention relates to the preparation of sulfonated triarylphosphines.

2. Description of the Prior Art:

It is known to this art that the sulfonated triarylphosphines are particularly useful as water-soluble ligands for forming complexes with transition metals, for example, rhodium, in water, and that such solutions may be used as catalysts, for example, for the synthesis of aldehyde compounds by the hydroformylation of olefins. Having regard to that use, the triarylphosphines must be in an excellent state of purity.

Various processes for the preparation of sulfonated triarylphosphines too are known to this art. In particular, same may be prepared by the sulfonation of aromatic rings by means of an $SO_3/H_2SO_4$ mixture, using a great excess thereof. The sulfonation reaction is then terminated by diluting the reaction medium with water. This results in a hydrolysate with a high sulfuric acid content, containing the sulfonated triarylphosphine in acid form.

In order to isolate the latter compound in the form of a neutral salt, the hydrolysate is neutralized, for example, with sodium hydroxide, in such manner as to eliminate the sulfate anions, by successive crystallization steps, in the form of sodium sulfate, in an aqueous medium, followed by crystallization of the sulfonated triarylphosphine in the form of its sodium salt by the addition of methanol thereto, followed by evaporation of the solvent.

Such a method suffers from several disadvantages. First of all, the neutralization operation is carried out with partial oxidation of the phosphine to phosphine oxide, that oxide being problematical insofar as it thus increases the amounts of inert diluent in the hydroformylation reaction. In addition, a substantial amount of sodium hydroxide is required for neutralization, having regard to the high proportion of $H_2SO_4$ in the hydrolysate. Consequently, a large amount of impurities is introduced by the sodium hydroxide. Now, those impurities, which then reappear in the final product, may be problematical from the point of view of catalysis. Among such impurities, chlorides also increase the danger of corrosion of the equipment in the subsequent aldehyde synthesis reaction. Moreover, the presence of sodium chlorate promotes the oxidation of triarylphosphine. The residual sodium sulfate from the neutralization operation is also problematical from the point of view of catalysis.

SUMMARY OF THE INVENTION

Accordingly, a major object of the present invention is the provision of an improved process for the preparation of a sulfonated triarylphosphine, in a high state of purity, and which improved process is conspicuously devoid of those disadvantages and drawbacks to date characterizing the state of this art.

Briefly, the improved process according to the invention features the preparation of sulfonated triarylphosphines or salts thereof having the following general formula:

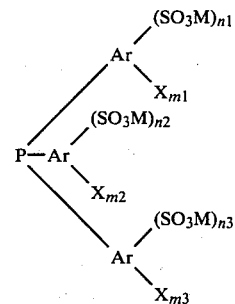

in which
the groups Ar are identical or different aryl radicals;
the radicals X are identical or different and are straight or branched chain alkyl or alkoxy radicals containing from 1 to 4 carbon atoms, hologen atoms, and the radicals hydroxy, nitrile, nitro, amino and amino substituted by straight or branched chain alkyl radicals containing from 1 to 4 carbon atoms;

M being $H^+$ or a selected cationic residue of organic or inorganic origin, such that the compound of formula (I) is soluble in water, formed from inorganic cations derived from alkali or alkaline earth metals or from the metals lead, zinc and copper; ammonium or quaternary ammonium ions;

$m_1$, $m_2$, $m_3$ are integers which are the same or different, ranging from 0 to 5;

$n_1$, $n_2$, $n_3$ are integers which are the same or different, ranging from 0 to 3, at least one of $n_1$, $n_2$ and $n_3$ being greater than or equal to 1;

which process comprising sulfonation of the aromatic rings of the corresponding triarylphosphine by means of a $H_2SO_4/SO_3$ admixture, then hydrolysis to terminate the reaction at the desired stage of sulfonation, thereby producing a sulfuric acid-rich hydrolysate comprising the sulfonated triarylphosphine;

and which process being characterized in that, in order to isolate the sulfonated triarylphosphine from said hydrolysate, in a first step, said hydrolysate is brought into contact with an organic phase comprising at least one extractant selected from the group comprising phosphoric or diphosphoric, phosphonic or diphosphonic, phosphinic or diphosphinic esters, phosphine oxides or diphosphine dioxides, slightly water miscible or immiscible $C_4$–$C_{12}$ alcohols and sulfoxides, then an aqueous raffinate is separated and an organic phase containing the sulfonated triarylphosphine is collected; next, in a second step, the sulfonated triarylphosphine is separated from the organic phase by means of a regeneration operation using water when M is $H^+$ or using an aqueous solution containing the element M in the other cases, and an aqueous solution of sulfonated triarylphosphine or salt thereof is recovered as the final product.

BRIEF DESCRIPTION OF THE DRAWING

The FIGURE of Drawing is a schematic/diagrammatic illustration of liquid/liquid extraction apparatus adopted to carry out the process according to the invention.

DETAILED DESCRIPTION OF THE INVENTION

More particularly, it will be appreciated that the process of the invention therefore makes it possible, prior to the neutralization operation, to effect separation of the sulfonated triarylphosphine and the sulfuric acid. In consequence, the amount of base to be introduced is considerably reduced and thus also is the amount of impurities introduced thereby.

The process of the invention therefore has the advantage in that it provides a product in a very high state of purity or else, for a given state of purity, in that it is possible to use a base of lower quality which is therefore less expensive.

Other features, details and objects of the invention will be more clearly apparent from the following description and the accompanying single FIGURE of Drawing which shows a diagrammatic view of a liquid/liquid extraction process, in one particular embodiment of the invention.

Among the phosphines of the formula (I), which are prepared by the process of the invention, preferred are those in which:

(i) The groups Ar are phenyl groups;

(ii) X represents an alkyl radical such as methyl and ethyl; an alkoxy radical such as methoxy and ethoxy; a chlorine atom;

(iii) The cationic residues M represent inorganic cations derived from metals such as sodium, potassium, calcium and barium; ammonium ions $NH_4^+$; quaternary ammonium ions such as tetramethylammonium, tetrapropylammonium, tetrabutylammonium;

(iv) $m_1$, $m_2$, $m_3$ are integers which are the same or different, ranging from 0 to 3.

More preferred are those phosphines of the formula (I), in which the groups Ar are phenyl groups; $m_1$, $m_2$ and $m_3$ are 0 and $n_1$, $n_2$ and $n_3$ are 0 or 1, the sum of $n_1+n_2+n_3$ ranging from 1 to 3.

In this latter group of compounds, especially preferred are the trisulfonated triphenylphosphines (TPPTS) ($n_1=n_2=n_3=1$), the $SO_3$ M groups being in the meta position and M being $Na^+$ or $H^+$.

The following are exemplary of the compounds of formula (I), which may be prepared in accordance with the present invention: alkali metal or alkaline earth metal salts, ammonium salts and quaternary ammonium salts of (m-sulfophenyl)diphenylphosphine; (p-sulfophenyl)diphenylphosphine; (m-sulfo, p-methylphenyl)-di(p-methylphenyl)phosphine; (m-sulfo, p-methoxyphenyl)di(p-methoxyphenyl)phosphine; (m-sulfo, p-chlorophenyl)di(chlorophenyl)phosphine; di(m-sulfophenyl)phenylphosphine; di(p-sulfophenyl)phenylphosphine; di(m-sulfo, p-methylphenyl)(p-methylphenyl)phosphine; di(m-sulfo, p-methoxyphenyl)(p-methoxyphenyl)phosphine; di(m-sulfo, p-chlorophenyl) (p-chlorophenyl)phosphine; tri(p-sulfophenyl)phosphine; tri(m-sulfo, p-methylphenyl)phosphine; tri(m-sulfo, p-methoxyphenyl)phosphine; tri(m-sulfo, p-chlorophenyl)phosphine; (o-sulfo, p-methylphenyl)(m-sulfo, p-methyl)(m,m'-disulfo, p-methyl)phosphine; (m-sulfophenyl)(m-sulfo, p-chlorophenyl)(m,m'-disulfo, p-chlorophenyl)phosphine.

The extracting agent or extractant, used in the subject process may be selected from the group comprising phosphoric or diphosphoric, phosphonic or diphosphonic, phosphinic or diphosphinic esters, and oxides of phosphines or dioxides of diphosphines, namely, compounds having the following general formula:

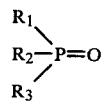

in which $R_1$, $R_2$ and $R_3$ are the same or different and may be, for example, straight or branched chain alkyl, alkenyl, alkynyl, alkoxyalkyl, aryl, and alkylaryl radicals, which radicals may be substituted by halogens, one or two or all of the groups $R_1$, $R_2$ and $R_3$ may be joined to the phosphorus atom by an oxygen atom, two of the groups $R_1$, $R_2$ and $R_3$ may be joined together and form a ring; or compounds having the following general formula:

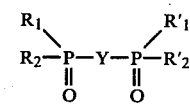

Y being a straight or branched chain alkylene group preferably comprising from 1 to 12 carbon atoms and $R'_1$ and $R'_2$ being defined in the same way as $R_1$ and $R_2$.

In particular, alkyl phosphates, such as, for example, tributylphosphate (TBP), triisobutylphosphate and trioctylphosphate, are representative extractants.

And exemplary of the extractants of the phosphonate type are the following: dibutyl butyl phosphonate (DBBP), 2-diethylhexyl (2-ethylhexyl) phosphonate (DEHEHP), bis(chloroethyl) vinyl phosphonate; diisobutyl butyl phosphonate; dipentyl pentyl phosphonate; dipentyl isopentyl phosphonate; diisopentyl isopentyl phosphonate; dihexyl hexyl phosphonate; dipentyl phenyl phosphonate; tetra-ethyl decylene diphosphonate; tetra-ethyl butylene diphosphonate; and tetra-isopropyl methyl methylene diphosphonate.

The extracting agents may also be of the phosphinate type, such as, for example, dioctylmethylphosphinate (DOMP), pentyl dipentyl phosphinate, and hexyl dihexylphosphinate.

Other suitable extractants comprise 1-oxo-1-octyloxy phosphole, 1-oxo-1-(2-ethylhexyl)-oxy phosphole and 1-oxo-1-dodecyloxy phosphole.

It is also possible to use phosphine oxides, such as, for example, oxides of di-n-hexylmethoxyoctylphosphine (DHMOPO), tri-n-butylphosphine (TBPO), trioctylphosphine (TOPO) and tri(2-ethylhexyl)phosphine.

The extractant may also be a $C_4-C_{12}$ alcohol, preferably a $C_8-C_{10}$ alcohol, for example, octanol, n-decanol, isodecanol or 2-ethylhexanol, or a sulfoxide, for example, n-decylmethylsulfoxide.

It will be appreciated that it would be possible to use a mixture of extractants, instead of a single extractant. In addition, in some cases, it may be advantageous to use an organic phase which comprises at least one extractant of the above-mentioned type, in solution in an inert diluent, for example, an aliphatic hydrocarbon.

The various stages in the process will now be described in greater detail.

The operations of sulfonation of the beginning phosphine and production of the hydrolysate are effected in per se known manner and the invention does not concern those stages.

It will be recalled, however, that the sulfonation operation may be carried out by means of an oleum containing 20% by weight of sulfuric anhydride, for example, at a temperature which may be between about 20° C. and 40° C. That sulfonation operation is carried out in the presence of a large excess of $H_2SO_4$.

When the sulfonation operation is to be terminated, water is poured into the mixture and the excess $SO_3$ is thus hydrolyzed.

The resulting hydrolysate therefore has a very high proportion of $H_2SO_4$, and it may have, for example, a concentration of $H_2SO_4$ on the order of 35 N.

It should also be noted that the hydrolysate contains a small amount of sulfonated triarylphosphine oxide.

In accordance with the invention, in a first step, the hydrolysate is then brought into intimate contact with an organic phase comprising an extractant of the type described hereinbefore.

It may be necessary to dilute the hydrolysate for the contacting operation. In that case, the diluting operation will be performed to such extent as to provide on the one hand good separation of the phases and on the other hand significant separation of the sulfonated triarylphosphine and sulfuric acid.

By way of example, when using TBP in general and also in particular in the case of preparing trisulfonated triphenylphosphine TPPTS with that extracting agent, the hydrolysate is diluted to a concentration in respect of sulfuric acid which may advantageously range from about 3 N to about 10 N, in particular from about 4 N to about 9 N and preferably from about 7 N to about 8 N.

The contacting of the hydrolysate with the organic phase is effected in per se known manner, more specifically continuously and countercurrently in a liquid/liquid extraction apparatus having a plurality of stages, of the mixer-settler or column type, for example.

The contacting of the organic phase with the hydrolysate is normally effected at ambient temperature. The temperature may also depend on the nature of the extractant employed.

Preferably, the contacting operation is carried out in an inert atmosphere, for example, in nitrogen. This avoids oxidation of the product sulfonated triarylphosphine into the corresponding phosphine oxide and, concomitantly, maintains or increases the process yields.

After the contacting operation has been performed, there is produced and separated an organic phase which contains the sulfonated triarylphosphine and a small amount of sulfuric acid which is also extracted, and an aqueous phase or raffinate which contains sulfuric acid. Moreover, it has been found that the major portion of the sulfonated triarylphosphine oxide present in the hydrolysate is not extracted by the organic extracting agent and remains in the aqueous phase. That result is particularly advantageous as it makes it possible to provide, upon completion of the process, a solution of sulfonated triarylphosphine having a very small amount of triarylphosphine oxide.

The second stage in the process of the invention comprises separating the sulfonated triarylphosphine from the organic phase.

The separation operation is effected by bringing the organic phase into contact with water in the case where M is $H^+$ or with an aqueous solution containing the aforesaid element M, in the other cases. In the latter case, that will be, for example, a solution of sodium hydroxide or potassium hydroxide, more particularly in a stoichiometric amount with respect to the sulfonated triarylphosphine and the co-extracted acid. In the same case, the phosphine is neutralized and converted into salt of the element M, and that salt goes back into the aqueous solution.

As for the extraction operation, the regeneration operation may be performed continuously and countercurrently with an identical piece of equipment. Thus, at the discharge from that stage, there is collected a purified organic phase and an aqueous phase comprising the sulfonated triarylphosphine in acid form or in the form of a salt, and which constitutes the desired final product. That solution may be used directly for aldehyde synthesis.

The aqueous regeneration solution used may be basic solutions in a high state of normality, for example, up to 6 N or 10 N, which facilitates the settling operation and makes it possible to produce solutions of sulfonated triarylphosphine having a high proportion, for example, up to 600 g of salt per liter.

By way of example, mention is made of preparing the sodium salt of TPPTS by regeneration with a solution of sodium hydroxide, at a level of concentration ranging from about 1 N to about 10 N.

It will be appreciated that the aqueous phase comprising the desired final product may comprise a certain amount of extractant, on the order of a few percent. In order to remove that extractant, it is possible for the aqueous phase to be treated with a water-immiscible inert organic solvent selected from saturated or aromatic hydrocarbons of the isooctane, toluene and kerosene type.

In order to reduce the proportion of sulfuric acid in the organic phase introduced in the regeneration step, it is advantageous for the organic phase to be washed by bringing it into contact with water or with an aqueous solution of a strong acid or one of its salts.

The washing operation may be effected in per se known manner, in particular continuously and countercurrently in a multi-stage liquid/liquid extraction apparatus. The aqueous phase resulting from the washing operation is conveyed to the extraction step.

In one particular embodiment of the invention, the aqueous washing phase used may be a portion of the solution of sulfonated triarylphosphine constituting the product obtained after the regeneration stage.

In order to further illustrate the present invention and the advantages thereof, the following specific examples are given, it being understood that same are intended only as illustrative and in nowise limitative.

EXAMPLE 1

This example describes a process for preparation of the hydrolysate.

200 g of sulfuric acid marketed by Rhone-Poulenc under the trademark Normapur (95% minimum) were introduced into a 500 ml Erlenmeyer flask. The flask was cooled to +6° C. by means of a water and an ice bath, under agitation. 100 g of triphenylphosphine Fluka purum (98% minimum) (TPP) were slowly introduced into the flask. When half of the TPP had been solubilized, the temperature in the sulfuric acid was allowed to rise again to complete the dissolution step.

1 liter of Nordhausen sulfuric acid, marketed under the trademark Prolabo (20% by weight $SO_3$) (1860 g) was introduced into a balloon flask which was disposed in a thermostatically controlled bath, and cooling to about +6° C. was effected, under agitation, by putting ice in the bath. When the above-mentioned temperature was reached, the solution of TPP/sulfuric acid was slowly poured therein over about 45 minutes. The temperature of the bath was regulated to 26° C. and the mixture was maintained for 90 hours in a slowly agitated condition, in a gentle flow of argon.

The temperature-controlled bath was cooled with ice as to provide a temperature of about +6° C. in the balloon flask, and 90 g of distilled water were poured therein over about 1 hour.

Obtained was a hydrolysate containing 2022 g of 100% sulfuric acid (89.83%), 37 g of water (1.65%) and 192 g of sulfonated triphenylphosphine.

EXAMPLE 2

The starting material was one liter of hydrolysate from the reaction mixture, produced in the manner described above in Example 1, containing 1712 g of $H_2SO_4$ and 116 g of sulfonated triphenylphosphine (TPPS). The liter of hydrolysate was diluted with 4 liters of water.

The solution was brought into contact with 1 liter of TBP and, after separation, the raffinate was again brought into contact with 1 liter of TBP. The raffinate from the second extraction operation contained 1.9 g of TPPS, namely, the extraction yield was higher than 98%.

The two fractions of extraction were combined and then regenerated with 250 cm$^3$ of 10 N sodium hydroxide, and a solution containing 130 g of sodium salt of TPPS and 129 g of sodium sulfate was collected.

EXAMPLE 3

The starting material was the same hydrolysate as in Example 2, and the operating procedure was also the same, but using instead one liter of n-octanol. The raffinate from the second extraction operation contained 5 g of TPPS, i.e., the yield of extraction was 95%.

The two fractions of extraction were combined and then regenerated with 250 cm$^3$ of 10 N sodium hydroxide, and a solution containing 125 g of the sodium salt of TPPTS and 250 g of sodium sulfate was collected.

EXAMPLE 4

This example illustrates carrying out the invention in a continuous process, and it is given with reference to the accompanying FIGURE of Drawing.

In an extraction battery 1 comprising 6 stages, a flow 2 of diluted hydrolysate, containing amounts of TPPS and $H_2SO_4$ of 30 g/l and 350 g/l, respectively, was transferred into the third stage. The flow rate of the flow 2 was 500 cm$^3$/h.

The battery was also supplied, countercurrently, with a flow 3 of TBP at a flow rate of 100 cm$^3$/h and a flow of water 4 at a flow rate of 20 cm$^3$/h, the latter providing for re-extraction of the sulfuric acid which was co-extracted with the TPPS by TBP.

A flow 5 exited from the battery 1, the flow 5 constituting the raffinate and contained 0.06 g/l and 335 g/l of TPPS and $H_2SO_4$, respectively.

A flow 6 of TBP charged with TPPS exited from the battery 1 and was transferred into a regeneration battery 7 which was also supplied, countercurrently, with a solution 8 of 1.05 N sodium hydroxide, at a flow rate of 85 cm$^3$/h.

A flow 9 of a solution of the sodium salt of TPPS, which constituted the desired final product, issued from the battery 7, at a flow rate of 102 cm$^3$/h. That solution contained 160 g/l of TPPS Na$_3$ and had a Na$_2$SO$_4$/TPPS Na$_3$ ratio of 100 ppm and a Cl-/TPPS Na$_3$ ratio of less than 50 ppm.

It is possible, in accordance with this embodiment of the invention, to tap off a portion of the flow 9, the tapped-off flow then constituting the flow 4 as feed for the battery 1.

EXAMPLE 5

This example employed apparatus of the same type as that used in Example 2.

Using a 4-stage extraction battery, a flow of diluted hydrolysate containing 350 g/l of $H_2SO_4$ and 5.37 10$^{-2}$ M/l of sulfonated triphenylphosphine was transferred into the second stage. The sulfonated triphenylphosphine was in the form of TPPTS, disulfonated triphenylphosphine TPPDS and sulfonated triphenylphosphine oxide OTPPS, in the respective percentages of 72.9%; 17.1%; 10% (percentage determined by NMR). The flow rate thereof was 500 cm$^3$/h.

The battery was also countercurrently charged with a flow of TBP at a flow rate of 110 cm$^3$/h and with a flow of water, at a rate of 20 cm$^3$/h.

From the battery issued an aqueous flow which constituted the raffinate and which contained 10$^{-3}$ M/l and 335 g/l, respectively, of TPPS and $H_2SO_4$.

Also issuing from the battery was a flow of TBP charged with TPPS, which was then transferred into a regeneration battery which was also supplied, countercurrently, with a 5.9 N sodium hydroxide solution, at a flow rate of 15 cm$^3$/h.

A flow of an aqueous solution of the sodium salt of TPPS, which constituted the desired final product, issued from the regeneration battery. The composition of that solution was as follows: TPPS: 0.85 M/l in the form of TPPTS, TPPDS, and diand tri-sulfonated triphenylphosphine oxides in the following respective percentages: 75.8%; 20.1%; 1.4%; 0.6%. The aqueous phase also contained 2.1% of TBP.

The TBP can be removed by a washing operation using a solvent as described hereinbefore.

It will be appreciated from this example that the process of the invention provides for effective elimination of the oxides of triphenylphosphines, which further contributes to enhancing the purity of the final product obtained.

EXAMPLE 6

The starting material used was the diluted hydrolysate of Example 2.

Four tests were successively carried out by contacting 1 liter of hydrolysate with, respectively, 1 liter of DBBP, 1 liter of dioctylmethylphosphinate (DOMP), 1 liter of tri-n-octylphosphine oxide (TOPO) diluted to 30% with Solvesso (Exxon trademark), and 1 liter of n-decylmethylsulfoxide (DMSO) diluted to 30% in Solvesso. After separation of the phases, the respective partition coefficients of $H_2SO_4$ and TPPS were determined ($P_{H_2SO_4}$—$P_{TPPS}$). These coefficients are reported in Table 1 below.

TABLE 1

| Extracting Agent | $P_{H_2SO_4}$ | $P_{TPPS}$ |
|---|---|---|
| DBBP | 0.27 | 50 |
| DOMP | 0.28 | 85 |
| TOPO | 0.10 | 10 |
| DMSO | 0.28 | 10 |

EXAMPLE 7

This example used a hydrolysate of the same type as that used in Example 2, which was diluted such as to vary its concentration in respect of sulfuric acid. The hydrolysate was extracted with TBP, with a ratio by volume between the phases of 1. The partition coefficients as determined after separation of the phases are reported in Table 2 below.

TABLE 2

| $H_2SO_4$ concentration of the hydrolysate | $P_{TPPS}$ | $P_{H_2SO_4}$ |
|---|---|---|
| 3 N | 6 | 0.04 |
| 4 N | 11 | 0.05 |
| 7 N | 58 | 0.1 |
| 8 N | 63 | 0.12 |
| 9 N | 15 | 0.15 |
| 10 N | 5 | 0.17 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a sulfonated triarylphosphine having the following general formula:

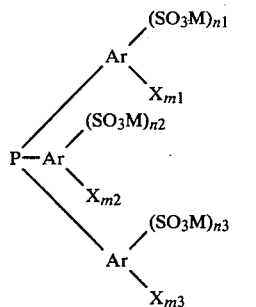

(I)

wherein the radicals Ar are identical or different aryl radicals, the radicals X are identical or different straight or branched chain alkyl or alkoxy radicals having from 1 to 4 carbon atoms, halogen atoms, and the radicals hydroxy, nitrile, nitro, amino and amino substituted by straight or branched chain alkyl radicals having from 1 to 4 carbon atoms; M is hydrogen or an organic or inorganic cation such that the compound having the formula (I) is soluble in water; $m_1$, $m_2$ and $m_3$ are integers which may be identical or different and which range from 0 to 5; and $n_1$, $n_2$ and $n_3$ are integers which may be identical or different and which range from 0 to 3, with the proviso that at least one of $n_1$, $n_2$ and $n_3$ is 1 or greater; comprising (i) sulfonating the aromatic moieties of a corresponding triarylphosphine starting material with an $H_2SO_4/SO_3$ mixture; (ii) hydrolyzing the sulfonation reaction mixture to terminate said sulfonation reaction when same has attained the desired degree of sulfonation, thereby producing a hydrolysate rich in sulfuric acid and which comprises the product sulfonated triarylphosphine; (iii) next liquid/liquid extracting said hydrolysate with an organic phase comprising at least one phosphoric or diphosphoric, phosphonic or diphosphonic, phosphinic or diphosphinic ester, or phosphine oxide or diphosphine dioxide, or slightly water miscible or immiscible $C_4$–$C_{12}$ alcohol, or sulfoxide extractant, whereby the sulfonated triarylphosphine (I) is extracted into said organic phase, (iv) separating the organic phase from the aqueous raffinate; (v) regenerating said organic phase with water when M is hydrogen or with an aqueous solution comprising M when M is other than hydrogen; and (vi) recovering an aqueous solution of said sulfonated triarylphosphine (I).

2. The process as defined by claim 1, wherein the sulfonated triarylphosphine (I), M is hydrogen, alkali or alkaline earth metal, lead, zinc, copper, ammonium or quaternary ammonium.

3. The process as defined by claim 2, wherein the sulfonated triarylphosphine (I), each Ar is phenyl, each X is alkyl, alkoxy or chloro, and $m_1$, $m_2$ and $m_3$ are integers ranging from 0 to 3.

4. The process as defined by claim 3, wherein the sulfonated triarylphosphine (I) $m_1$, $m_2$ and $m_3$ are 0 and $n_1$, $n_2$ and $n_3$ are 0 or 1, with the sum of $n_1+n_2+n_3$ ranging from 1 to 3.

5. The process as defined by claim 1, wherein the extractant comprises a compound having the following general formula:

(II)

wherein $R_1$, $R_2$ and $R_3$, which may be identical or different, are straight or branched chain alkyl, alkenyl, alkynyl, alkoxyalkyl, aryl or alkylaryl radicals, or halogen substituted such radicals, with the proviso that any one or more of such radicals may be joined to the phosphorus atom via an oxygen atom bridge, and with the further proviso that any two of $R_1$, $R_2$ and $R_3$ may together be a single divalent radical to form a ring moiety.

6. The process as defined by claim 1, wherein the extractant comprises a compound having the following general formula:

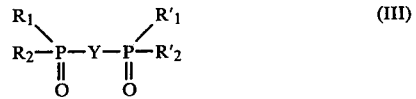

(III)

wherein Y is a straight or branched chain alkylene radical, and $R_1$, $R_2$, $R'_1$ and $R'_2$, which may be identical or different, are straight or branched chain alkyl, alkenyl, alkynyl, alkoxyalkyl, aryl or alkylaryl radicals, or halogen substituted such radicals, with the proviso that any one or more of such radicals may be joined to the phosphorus atom via an oxygen atom bridge, and with the further proviso that either $R_1$ and $R_2$ or $R'_1$ and $R'_2$ may together be a single divalent radical to form a ring moiety.

7. The process as defined by claim 1, wherein the extractant comprises tributylphosphate, triisobutylphosphate, trioctylphosphate, dibutyl butyl phosphonate (DBBP), 2-diethylhexyl (2-ethylhexyl) phosphonate (DEHEHP), bis(chloroethyl) vinyl phosphonate, diisobutyl butyl phosphonate, dipentyl pentyl phosphonate, dipentyl isopentyl phosphonate, diisopentyl isopentyl phosphonate, dihexyl hexyl phosphonate, dipentyl phenyl phosphonate, tetra-ethyl decylene diphosphonate, tetra-ethyl butylene diphosphonate, tetra-isopropyl methyl methylene diphosphonate, dioctylmethylphosphinate (DOMP), pentyl dipentyl phosphinate, hexyl dihexylphosphinate, 1-oxo-1-octyloxy phosphole, 1-oxo-1-(2-ethylhexyl)-oxy phosphole, 1-oxo-1-dodecyloxy phosphole, di-n-hexylmethoxyoctylphosphine oxide (DHMOPO), tri-n-butylphosphine oxide (TBPO), trioctylphosphine oxide (TOPO) or tri(2-ethylhexyl)phosphine oxide.

8. The process as defined by claim 1, wherein the extractant comprises tributylphosphate, dibutyl butyl phosphonate, dioctylmethylphosphinate or trioctylphosphine oxide.

9. The process as defined by claim 1, wherein the extractant comprises a $C_4$–$C_{12}$ alcohol.

10. The process as defined by claim 1, wherein the extractant comprises a $C_8$–$C_{10}$ alcohol.

11. The process as defined by claim 10, wherein the extractant comprises octanol.

12. The process as defined by claim 1, wherein the extractant comprises a sulfoxide.

13. The process as defined by claim 12, wherein the extractant comprises n-decylmethylsulfoxide.

14. The process as defined by claim 1, further comprising, prior to the regeneration step (v), washing said separated organic phase with water or an aqueous solution of a strong acid or salt thereof.

15. The process as defined by claim 14, said wash solution comprising a fraction of the aqueous solution final product.

16. The process as defined by claim 1, said steps (iii) and (v) being carried out continuously and countercurrently.

17. The process as defined by claim 14, said steps (iii) and (v) and said washing step being carried out continuously and countercurrently.

18. The process as defined by claim 1, further comprising diluting said hydrolysate prior to the liquid/liquid extraction step (iii).

19. The process as defined by claim 18, said hydrolysate being diluted to an $H_2SO_4$ concentration ranging from 3 N to 10 N, and the extractant comprising tributylphosphate.

20. The process as defined by claim 19, said hydrolysate being diluted to an $H_2SO_4$ concentration ranging from 4 N to 9 N.

21. The process as defined by claim 20, said hydrolysate being diluted to an $H_2SO_4$ concentration ranging from 7 N to 8 N.

22. The process as defined by claim 1, said aqueous regenerating solution comprising a solution of sodium hydroxide.

23. The process as defined by claim 1, further comprising washing said final product aqueous solution with a water-immiscible inert organic solvent.

24. The process as defined by claim 1, further comprising carrying out said liquid/liquid extraction step (iii) in an inert atmosphere.

25. The process as defined by claim 1, wherein the hydrolyzing step (ii) of the sulfonation reaction mixture is carried out with water.

* * * * *